US012657760B2

(12) United States Patent
Kronman et al.

(10) Patent No.: US 12,657,760 B2
(45) Date of Patent: Jun. 16, 2026

(54) SYSTEM AND METHOD FOR DETERMINING TOOL POSITIONING, AND FIDUCIAL MARKER THEREFORE

(71) Applicant: Visionsense Ltd., Petah Tikva (IL)

(72) Inventors: Achia Kronman, Pardes Hannah (IL); Rami Cohen, Misgav Regional Council (IL); Ohad Doron, Herzelia (IL); Amit Ruf, Hod Hasharon (IL); Daniella Ziv, Tel Aviv (IL); Elisha Rabinovitz, Haifa (IL); Gaetan Guerin, Lyons (FR); Tal Davidson, Yokneam (IL)

(73) Assignee: Visionsense Ltd., Petah Tikva (IL)

( * ) Notice: Subject to any disclaimer, the term of this patent is extended or adjusted under 35 U.S.C. 154(b) by 170 days.

(21) Appl. No.: 17/922,985

(22) PCT Filed: May 25, 2021

(86) PCT No.: PCT/IL2021/050615
§ 371 (c)(1),
(2) Date: Nov. 3, 2022

(87) PCT Pub. No.: WO2021/245649
PCT Pub. Date: Dec. 9, 2021

(65) Prior Publication Data
US 2023/0233272 A1     Jul. 27, 2023

Related U.S. Application Data

(60) Provisional application No. 63/033,621, filed on Jun. 2, 2020.

(51) Int. Cl.
| | |
|---|---|
| *G06T 7/73* | (2017.01) |
| *A61B 17/072* | (2006.01) |
| *A61B 18/00* | (2006.01) |
| *A61B 34/30* | (2016.01) |
| *G06V 10/24* | (2022.01) |

(52) U.S. Cl.
CPC .......... *G06T 7/73* (2017.01); *A61B 17/07207* (2013.01); *A61B 34/30* (2016.02); *G06V 10/245* (2022.01); *A61B 2018/0063* (2013.01)

(58) Field of Classification Search
CPC ..... G06T 7/73; A61B 34/30; A61B 17/07207; A61B 2018/0063; G06V 10/245
See application file for complete search history.

(56) References Cited

U.S. PATENT DOCUMENTS

| | | | |
|---|---|---|---|
| 2010/0168562 A1 | 7/2010 | Zhao et al. | |
| 2012/0209288 A1* | 8/2012 | Robinson ........... | A61B 18/1445 606/130 |

(Continued)

FOREIGN PATENT DOCUMENTS

| | | | | |
|---|---|---|---|---|
| EP | 2391290 B1 | 2/2020 | | |
| WO | WO-2018218175 A1 * | 11/2018 | ........... | G09B 23/285 |

OTHER PUBLICATIONS

Peace, J., et al., "E2ETag: An End-to-End Trainable Method for Generating and Detecting Fiducial Markers," University of Nebraska-Lincoln. 2020. p. 1-12 (Year: 2020).*

(Continued)

*Primary Examiner* — Sean A Frith
(74) *Attorney, Agent, or Firm* — Carter, DeLuca & Farrell, LLP

(57) ABSTRACT

A spatial orientation determining system includes an imaging device configured for obtaining an image of a surgical site, a surgical tool defining a central axis, a processor, and a memory. The surgical tool configured for operating at the surgical site and disposed thereon, a fiducial marker generated by a machine learning network. The fiducial marker includes a distinct pattern. The memory, includes instructions which when executed by the processor, cause the system to: access an image from the imaging device, the image including a portion of the fiducial marker; determine (Continued)

a spatial positioning of the surgical tool based on at least a visible portion of the fiducial marker and the distinct pattern; and determine, based on the spatial positioning, a positioning, an orientation, and/or a rotational angle of the surgical tool.

15 Claims, 10 Drawing Sheets

(56) References Cited

U.S. PATENT DOCUMENTS

| | | | | |
|---|---|---|---|---|
| 2017/0340367 | A1 | 11/2017 | Beger et al. | |
| 2018/0311012 | A1* | 11/2018 | Moctezuma | A61B 34/20 |
| 2019/0325574 | A1* | 10/2019 | Jin | G06V 10/454 |

OTHER PUBLICATIONS

Garrido-Jurado, S., et al., "Automatic generation and detection of highly reliable fiducial markers under occlusion," Pattern Recognition. vol. 47, 2014. p. 2280-2292 (Year: 2014).*

Grinchuk, O., et al., Learnable Visual Markers, 30th Conference on Neural Information Processing Systems, 2016. p. 1-9 (Year: 2016).*
International Search Report mailed Sep. 21, 2021 and Written Opinion completed Sep. 8, 2021 corresponding to counterpart Int'l Patent Application PCT/IL2021/050615.
Manuel Katanacho et al, "Surgical navigation with QR codes", Current Directions in Biomedical Engineering, vol. 2, No. 1, Sep. 1, 2016 (Sep. 1, 2016), p. 355-358, XP055450544, DOI: 10.1515/cdbme-2016-0079 external link. Relevant to Claim Nos. 1-20.
Qian Long et al, "ARssist: augmented reality on a head-mounted display for the first assistant in robotic surgery", Healthcare Technology Letters, vol. 5, No. 5, Sep. 2018 (Sep. 2018), p. 194-200, XP006076212, DOI: 10.1049/HTL.2018.5065 external link. Relevant to Claim Nos. 1-20.
Webpage The 31st British Machine Vision Virtual Conference on Sep. 7-10, 2020 (<https://www.bmvc2020-conference.com>).
Peace, et al., "E2ETag: An End-to-End Trainable Method for Generating and Detecting Fiducial Markers" (2020) (<https://www.bmvc2020-conference.com/assets/papers/0890.pdf>).
Examination Report issued in corresponding application EP 21735420.8 dated Feb. 19, 2025 (7 pages).
First Chinese Office Action issued in corresponding Chinese Application No. 202180040046.4 dated Oct. 25, 2025, 14 pages.

\* cited by examiner

600

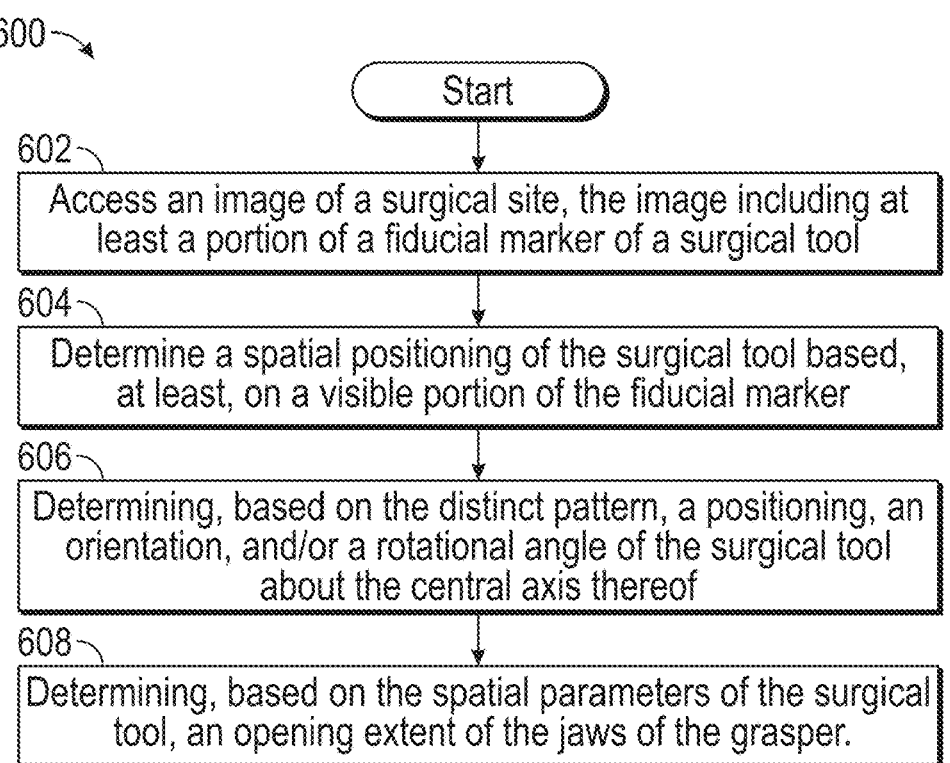

Start

602 — Access an image of a surgical site, the image including at least a portion of a fiducial marker of a surgical tool 604 — Determine a spatial positioning of the surgical tool based, at least, on a visible portion of the fiducial marker 606 — Determining, based on the distinct pattern, a positioning, an orientation, and/or a rotational angle of the surgical tool about the central axis thereof 608 — Determining, based on the spatial parameters of the surgical tool, an opening extent of the jaws of the grasper.

FIG. 6

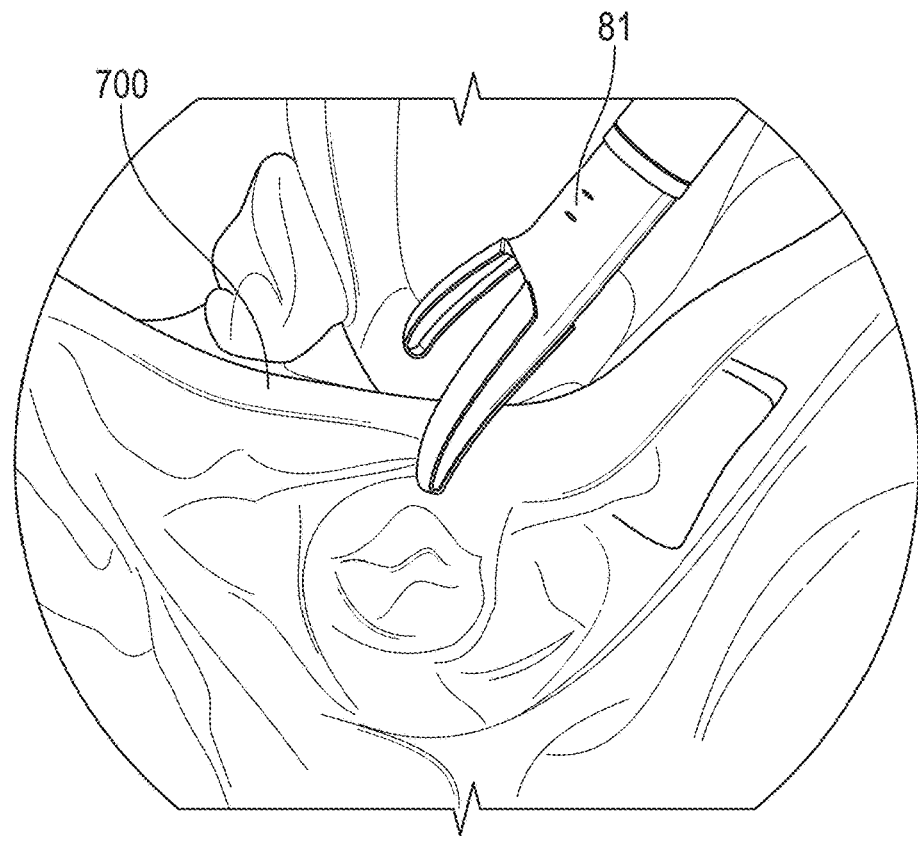

FIG. 7

Input Frame

ICG Labeling

SYSTEM AND METHOD FOR DETERMINING TOOL POSITIONING, AND FIDUCIAL MARKER THEREFORE

CROSS-REFERENCE TO RELATED APPLICATIONS

The present application is a U.S. National Stage Application filed under 35 U.S.C. § 371(a) claiming the benefit of and priority to International Patent Application No. PCT/IL2021/050615, filed May 25, 2021, which claims the benefit of and priority to U.S. Provisional Patent Application Ser. No. 63/033,621, filed Jun. 2, 2020, the entire disclosures of each of which being incorporated by reference herein.

FIELD

This disclosure relates generally to surgical tools, in particular, determining the spatial positioning of tools used in laparoscopic surgery.

BACKGROUND

Endoscopic instruments have become widely used by surgeons in endoscopic surgical procedures because they enable surgery to be less invasive as compared to conventional open surgical procedures in which the surgeon is required to cut open large areas of body tissue. As a direct result thereof, endoscopic surgery minimizes trauma to the patient and reduces patient recovery time and hospital costs.

In standard endoscopic procedures, an endoscope or laparoscope is being used to view the surgical field and working tools are used to perform the surgery. Such tools usually consist of external handle through which the surgeon operates the tool, a connecting shaft and end effector that may include graspers, clamps scissors, staplers needle holders, vessel sealing devices and more.

An endoscopic camera communicating with an operating room display is also often utilized in endoscopic surgery to enable the surgeon to visualize the surgical site as the end effector assembly is maneuvered into position and operated to perform the desired surgical task. In this type of operations, the surgeon cannot rely on eye-mind-hand coordination. Special training is required to compensate for the different sensory perception and the limited degrees of freedom of the laparoscopic instruments. Determining tool positioning has the following challenges, for example, light changes, shadows, specular reflections, noise, motion blur in the images, and/or viewing angles.

Accordingly, a continuing need exists for determining tool spatial positioning in a surgical image.

SUMMARY

In accordance with the disclosure, a spatial orientation and dimension determining system is presented. The spatial orientation and dimension determining system includes an imaging device configured for obtaining an image of a surgical site, a surgical tool defining a central axis, a processor, and a memory. The surgical tool is configured for operating at a surgical site and disposed thereon, is a fiducial marker generated by a machine learning network. The fiducial marker includes a distinct pattern. The memory, includes instructions which when executed by the processor, cause the spatial orientation and dimension determining system to access an image from the imaging device, the image including at least a portion of the fiducial marker;

determine a spatial positioning of the surgical tool based on a visible portion of the fiducial marker and the distinct pattern; and determine, based on spatial parameters of the surgical tool, a position, a dimension, and/or an orientation of the surgical tool.

In an aspect, the surgical tool is an endoscopic surgical tool, having a functional extension configured to perform a surgical function. The functional extension may include a grasper, stapler, and/or vessel sealer. The functional extension may include jaws.

In an aspect, the instructions, when executed by the processor, may further cause the system to: determine an opening extent of the functional extension based on the determined position, dimension, and/or orientation of the surgical tool and determine, based on the opening extent of the jaws of the functional extension, an amount of tissue pinched between the jaws of the functional extension, and/or the extent to which the tissue is clamped between the jaws of the functional extension.

In another aspect, the functional extension has a first, fixed jaw which may define a plane and a second, movable jaw which moves relative to the plane.

In an aspect, the surgical tool may further include a shaft having a longitudinal axis, the surgical tool being configured at least for revolution about the central axis and including at least one fiducial marker located on the shaft.

The instructions, when executed by the processor, may further cause the spatial orientation determining system to extract at least any one of the following physical quantities: jaw opening, distance to an endoscope, distances along the shaft, and/or distances orthogonal to the shaft.

In another aspect, the fiducial marker may extend along a curved outer surface the shaft about the central axis, such that an image of the surgical tool reveals only a portion of the fiducial marker.

In yet another aspect, the portion of the fiducial marker may be sufficient for determining the spatial positioning of the surgical tool.

In still yet another aspect, the fiducial marker may include a fixed point corresponding to a known point of the surgical tool, whereby identifying the portion of the fiducial marker visible to the imaging device allows for the determining of the orientation of the surgical tool.

In still yet another aspect, the fiducial marker may have a unique arrangement of of color, size, clustering, color gradient, and/or protrusion.

In another aspect, the fiducial marker may include a pattern of four-by-four squares of different characteristics.

In accordance with aspects of the disclosure, a surgical tool configured for operating at a surgical site is presented. The surgical tool includes a grasper including jaws and, disposed thereon, at least one fiducial marker generated by a machine learning network. The at least one fiducial marker includes a distinct pattern.

In an aspect, the surgical tool may further include at least one functional extension configured to perform a surgical function.

In another aspect, the at least one functional extension may be a bowel grasper, a stapler, and/or a vessel sealer.

In yet another aspect, the fiducial marker may include an image and/or a pattern configured to be recognizable by a software analyzing the image obtained by an imaging device.

In still yet another aspect, the fiducial marker may have a unique arrangement of color, size, clustering, color gradient, and/or protrusion.

In still yet another aspect, the surgical tool further may include a shaft defining a central axis. The fiducial marker may extend along the shaft about the central axis, such that an image of the surgical tool reveals only a portion of the fiducial marker.

In still yet another aspect, the portion of the fiducial marker may be sufficient for determining a spatial positioning of the surgical tool.

In still yet another aspect, the fiducial marker may include a pattern of four-by-four squares of different characteristics.

In still yet another aspect, the fiducial marker may be in the form of a QR code.

In accordance with other aspects of the disclosure, a fiducial marker configured for use in combination with the surgical tool. The fiducial marker may have a unique pattern configured for recognition by a processing unit for determining a spatial orientation of the surgical tool.

BRIEF DESCRIPTION OF DRAWINGS

Various aspects of the disclosure are described herein with reference to the drawings wherein:

FIG. 6 is a flow diagram of a method for spatial orientation of a surgical tool of the system of FIG. 1 in accordance with the disclosure;

FIG. 7 is an image of a bowel grasper during surgery in accordance with the disclosure;

Figure 1:
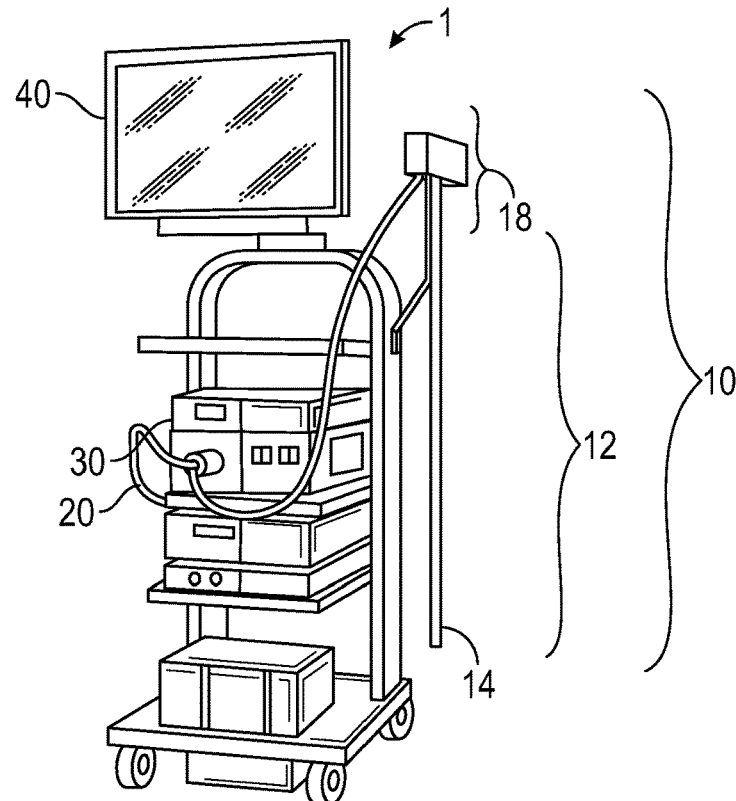
FIG. 1 is a diagram of an exemplary visualization or endoscope system in accordance with the disclosure.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION

The disclosed surgical device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

This disclosure relates generally to surgical tools, in particular, determining the spatial positioning of tools used in laparoscopic or robotic surgery.

Embodiments of the presently disclosed devices, systems, and methods of treatment are described in detail with reference to the drawings, in which like reference numerals designate identical or corresponding elements in each of the several views. As used herein, the term "distal" refers to that portion of a structure that is farther from a user, while the term "proximal" refers to that portion of a structure that is closer to the user. The term "clinician" refers to a doctor, nurse, or other care provider and may include support personnel.

The disclosure is applicable where images of a surgical site are captured. Endoscope systems are provided as an example, but it will be understood that such description is exemplary and does not limit the scope and applicability of the disclosure to other systems and procedures.

Figure 2:
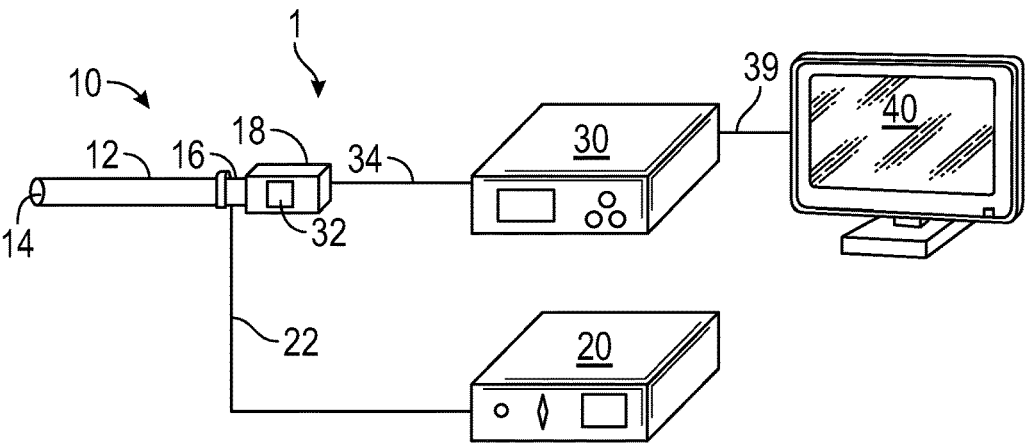
FIG. 2 is a schematic configuration of the visualization or endoscope system of FIG. 1.
Figure 3:
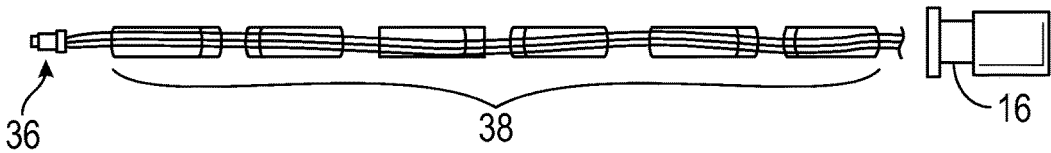
FIG. 3 is a diagram illustrating another schematic configuration of an optical system of the system of FIG. 1.

Referring initially to FIGS. 1-3, an endoscope system 1, in accordance with the disclosure, includes an endoscope 10, a light source 20, a video system 30, and a display device 40. With continued reference to FIG. 1, the light source 20, such as an LED/Xenon light source, is connected to the endoscope 10 via a fiber guide 22 that is operatively coupled to the light source 20 and to an endocoupler 16 disposed on, or adjacent to, a handle 18 of the endoscope 10. The fiber guide 22 includes, for example, fiber optic cable which extends through the elongated body 12 of the endoscope 10 and terminates at a distal end 14 of the endoscope 10. Accordingly, light is transmitted from the light source 20, through the fiber guide 22, and emitted out the distal end 14 of the endoscope 10 toward a targeted internal feature, such as tissue or an organ, of a body of a patient. As the light transmission pathway in such a configuration is relatively long, for example, the fiber guide 22 may be about 1.0 m to about 1.5 m in length, only about 15% (or less) of the light flux emitted from the light source 20 is outputted from the distal end 14 of the endoscope 10.

With reference to FIGS. 2 and 3, the video system 30 is operatively connected to an image sensor 32 mounted to, or disposed within, the handle 18 of the endoscope 10 via a data cable 34. An objective lens 36 is disposed at the distal end 14 of the elongated body 12 of the endoscope 10 and a series of spaced-apart, relay lenses 38, such as rod lenses, are positioned along the length of the elongated body 12 between the objective lens 36 and the image sensor 32. Images captured by the objective lens 36 are forwarded through the elongated body 12 of the endoscope 10 via the relay lenses 38 to the image sensor 32, which are then communicated to the video system 30 for processing and output to the display device 40 via cable 39. The image sensor 32 is located within, or mounted to, the handle 18 of the endoscope 10, which can be up to about 30 cm away from the distal end 14 of the endoscope 10.

Figures 4, 5:
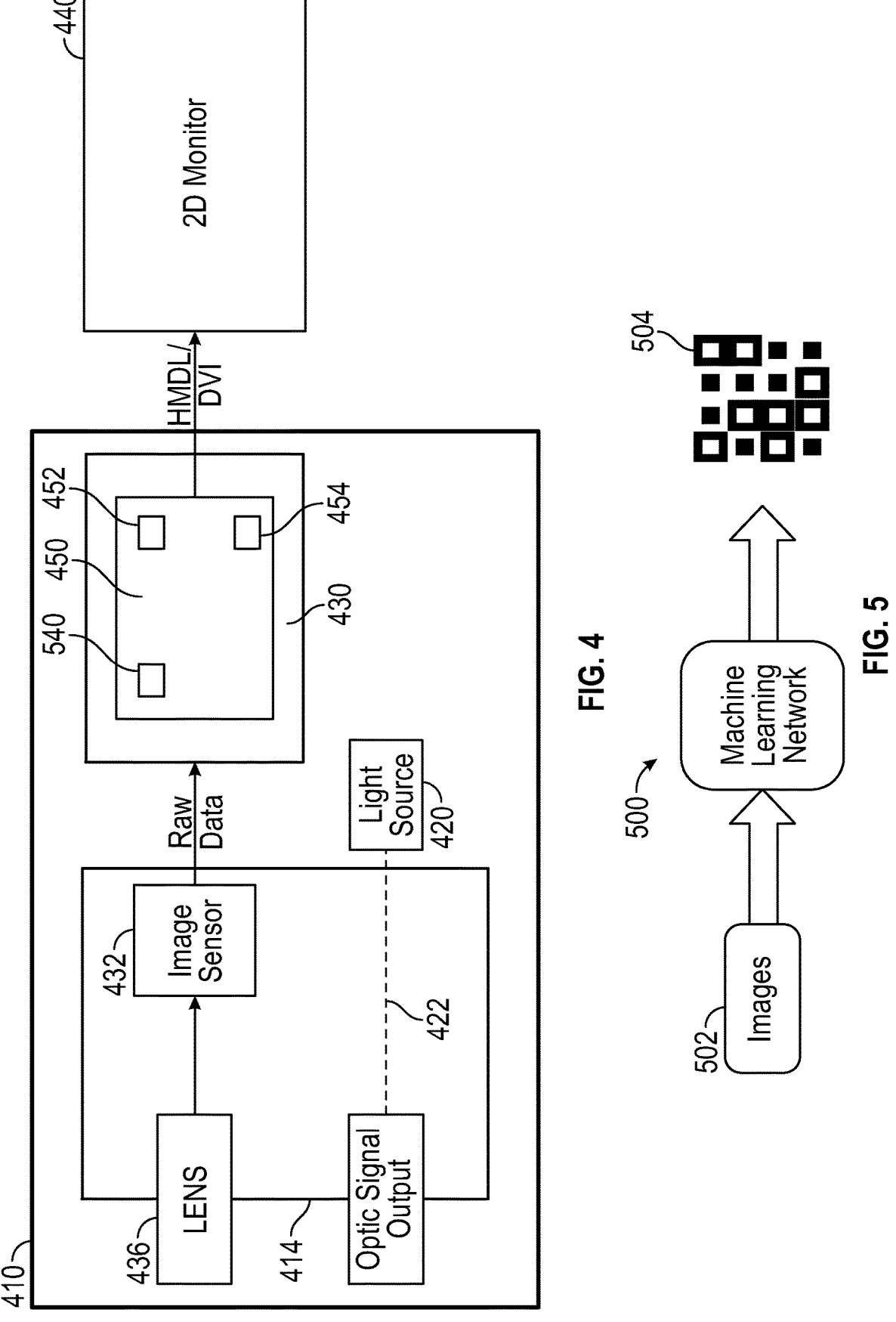
FIG. 4 is a schematic configuration of the visualization or endoscope system in accordance with an aspect of the disclosure.
FIG. 5 is a block diagram of a machine learning network for generating fiducials in accordance with the disclosure.

Referring to FIG. 4, there is shown a schematic configuration of a system, which may be the endoscope system of FIG. 1 or may be a different type of system (e.g., visualization system, etc.). The system, in accordance with the disclosure, includes an imaging device 410, a light source 420, a video system 430, and a display device 440. The light source 420 is configured to provide light to a surgical site through the imaging device 410 via the fiber guide 422. The distal end 414 of the imaging device 410 includes an objective lens 436 for receiving or capturing the image at the surgical site. The objective lens 436 forwards or transmits the image to the image sensor 432. The image is then communicated to the video system 430 for processing. The video system 430 includes an imaging device controller 450 for controlling the endoscope and processing the images. The imaging device controller 450 includes a processor 452 connected to a computer-readable storage medium or a memory 454 which may be a volatile type memory, such as RAM, or a non-volatile type memory, such as flash media, disk media, or other types of memory. In various embodiments, the processor 452 may be another type of processor such as, without limitation, a digital signal processor, a microprocessor, an ASIC, a graphics processing unit (GPU), field-programmable gate array (FPGA), or a central processing unit (CPU).

In various embodiments, the memory 454 can be random access memory, read only memory, magnetic disk memory, solid state memory, optical disc memory, and/or another type of memory. In various embodiments, the memory 454 can be separate from the imaging device controller 450 and can communicate with the processor 452 through communication buses of a circuit board and/or through communication cables such as serial ATA cables or other types of cables. The memory 454 includes computer-readable instructions that are executable by the processor 452 to operate the imaging device controller 450. In various embodiments, the imaging device controller 450 may include a network interface 540 to communicate with other computers or a server.

FIG. 5 shows a block diagram for a machine learning network 500 for generating a fiducial marker 504, in accordance with the disclosure. In aspects, the machine learning network 500 may generate a fiducial marker 504 based on image data 502. The image data may include training images. The machine learning network 500 may optimize the fiducial marker 504 such that it is easier to read in an image of a surgical site. The machine learning network 500 may include, for example, a convolutional neural network (CNN), and/or a recurrent adversarial network. For example, given a training data set, the recurrent adversarial network learns to generate new data with the same statistics as the training data set. Other training techniques may be used.

In machine learning, a CNN is a class of artificial neural network (ANN), most commonly applied to analyzing visual imagery. The convolutional aspect of a CNN relates to applying matrix processing operations to localized portions of an image, and the results of those operations (which can involve dozens of different parallel and serial calculations) are sets of many features that are used to train neural networks. A CNN typically includes convolution layers, activation function layers, and pooling (typically max pooling) layers to reduce dimensionality without losing too many features. Additional information may be included in the operations that generate these features. Providing unique information that yields features that give the neural network information can be used to ultimately provide an aggregate way to differentiate between different data input to the neural networks.

The terms "artificial intelligence," "data models," or "machine learning" may include, but are not limited to, neural networks, CNNs, recurrent neural networks (RNN), generative adversarial networks (GAN), Bayesian Regression, Naive Bayes, nearest neighbors, least squares, means, and support vector regression, among other data science and artificial science techniques.

The fiducial marker 504 may include a set of shapes, or figures, an image and/or a distinct pattern, configured to be recognizable by a software analyzing the image obtained by the endoscope 10, in such a way that any combination of them visible to a camera will be sufficient to localize the fiducial compare to the camera (distance, angle, and/or orientation). Any two shapes or figures or patterns visible to the camera will be enough for localization. However, for higher accuracy, more than two may be used. For example, the fiducial marker 504 may include a unique pattern of four-by-four squares, e.g., selectively colored black and white. In another example, the pattern may resemble a simplified QR code (see, e.g., FIG. 5). It should be understood that various designs of the fiducial marker 504 may be used, so long as images of the fiducial marker 504 taken at different angles are unique and recognizable by the software. In aspects, fiducial marker 504 may have a unique arrangement of color, size, clustering, color gradient, In one aspect, the fiducial can be applied to the distal portion of the shaft of the surgical tool, most visible to the imaging system. Yet the fiducial may be applied to any portion of the tool that is visible to the imaging system. The fiducial can be applied in any technology that can attach or printed by any printing method and/or protrusion. Printing methods may include but are not limited to laser printing, ink printing, 3D printing and/or painting the fiducial on a surgical tool configured for operating at the surgical site.

With reference to FIG. 6, the flow diagrams include various blocks described in an ordered sequence. However, those skilled in the art will appreciate that one or more blocks of the flow diagram may be performed in a different order, repeated, and/or omitted without departing from the scope of the disclosure. The below description of the flow diagram refers to various actions or tasks performed by one or more video system 30, but those skilled in the art will appreciate that the video system 30 is exemplary. In various embodiments, the disclosed operations can be performed by another component, device, or system. In various embodiments, the video system 30 or other component/device performs the actions or tasks via one or more software applications executing on a processor. In various embodiments, at least some of the operations can be implemented by firmware, programmable logic devices, and/or hardware circuitry. Other implementations are contemplated to be within the scope of the disclosure.

Initially, at step 602, the video system 30 accesses an image from the imaging device (e.g., endoscope 10). The image includes at least a portion of the fiducial marker 504 (FIG. 5) of a surgical tool configured for operating at the surgical site. For example, the image may show only a square of 2×2 patterns at the top or at the bottom quarter of the fiducial marker 504. In aspects, the image may include at least two shapes, figures, and/or patterns composing the fiducial marker 504.

The fiducial marker 504 may include an image and/or a distinct pattern configured to be recognizable by a software analyzing the image obtained by the endoscope 10. For example, the fiducial marker 504 may include a unique pattern of four-by-four squares, e.g., selectively colored black and white. In another example, the pattern may resemble a simplified QR code (see, e.g., FIG. 5). It should be understood that various designs of the fiducial marker 504 may be used, so long as images of the fiducial marker 504 taken at different angles are unique and recognizable by the software. In aspects, fiducial marker 504 may have a unique arrangement of color, size, clustering, color gradient, printing method, and/or protrusion. Printing methods may include but are not limited to laser printing, ink printing, and/or 3D printing.

In aspects, the fiducial marker may be generated by a machine learning network 500. For example, the machine learning network may include a neural network, a support vector machine (SVM), and/or a recurrent adversarial network. The fiducial marker may be generated by the machine learning network, the fiducial marker optimized for imaging by the imaging device. For example, optimization may be based on one or more characteristics of images used to train the machine learning network. Generally, during training, patterns, and relationships in the data are identified to build a model. For example, machine learning networks then make inferences from characteristics of images based on the model.

Next, at step 604, the video system 30 determines a spatial positioning of the surgical tool 80 based, at least, on a visible portion of the fiducial marker 504. In aspects, the fiducial marker 504 may extend along a curved outer surface the shaft 86 (FIG. 8) of the surgical tool 80, about the central axis, such that an image of the surgical tool 80 reveals only a portion of the fiducial marker 504. For example, a portion of the fiducial marker is sufficient for determining the spatial positioning of the surgical tool (see, e.g., FIG. 12). A fixed point of the fiducial marker 504 is corresponding to a known point of the surgical tool 80, whereby identifying the portion of the fiducial marker 504 visible to the endoscope 10 (e.g., imaging device) allows for the determining of the orientation of the surgical tool 80.

Next, at step 606, the video system 30 determines, based on the distinct pattern, a dimension, a positioning, an orientation, and/or a rotational angle of the surgical tool 80 about the central axis thereof. For example, the video system 30 may determine, based on the distinct pattern of the fiducial marker 504, that the surgical tool 80 is rotated about 90 degrees about the central axis thereof. In aspects, the video system 30 may determine, based on the distinct pattern, a dimension, a positioning, and/or an orientation of, for example, tissue adjacent to the surgical tool, such as, but not limited to, an opening extent of the jaws of a grasper, and/or the diameter of the vessel to be sealed by a power delivery device (e.g., a vessel sealer).

Next, at step 608, the video system 30 determines an opening extent of the jaws of the grasper based on spatial parameters of the surgical tool 80. For example, the video system 30 may determine that the jaws are open about 5 mm. In aspects, the video system 30 may determine, based on the opening extent of the jaws of a functional extension 81 (e.g., a stapler), an amount of tissue pinched between the jaws 82,

84 of the functional extension 81, and/or the extent to which the tissue is clamped between the jaws 82, 84 of the functional extension 81. For example, the determination of tissue thickness may be used to determine how much electrosurgical energy to apply to the pinched tissue. In aspects, the video system 30 may determine the dimensions and/or orientations of all parts of the tool and/or the tissue in the vicinity of any part of the surgical tool. The functional extension 81 may include any end effector with known dimensions, for example, but not limited to, a grasper, a stapler, and/or a vessel sealer.

In aspects, the surgical tool includes a shaft having a longitudinal axis. The surgical tool being configured at least for revolving about the central axis. In aspects, the surgical tool may include a fiducial marker located on the shaft. In aspects, the video system 30 may extract the following physical quantities: jaw opening, distance to an endoscope, distances along the shaft, and/or distances orthogonal to the shaft. The extracted physical quantities may be used to determine the size of objects in the image, such as, but not limited to organs, and/or surgical tools. For example, based on the extracted physical quantities, the jaws may be used as a virtual tape measure device. In aspects, an edge of the functional extension 81 (e.g., the end effector) may define a plane perpendicular to the central axis on which a radial distance measurement of objects on that plane relative to the edge can be established.

In aspects, the video system 30 may detect the presence and/or model of the surgical tool based on the fiducial marker. Based on the known model of the surgical tool, a 3D reconstruction may be made by the video system 30.

FIG. 7 an image of a bowel grasper 81 is shown during surgery, about to pinch a portion of the tissue 700 of a patient.

Figure 8:
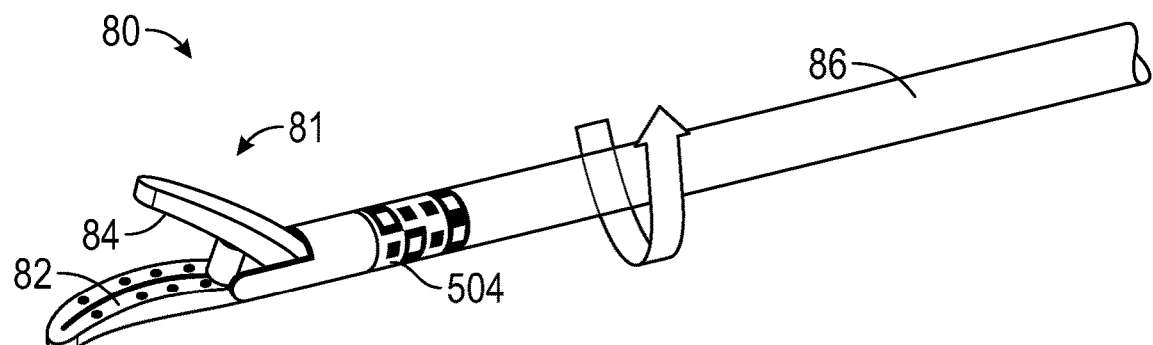
FIG. 8 is a perspective view of a bowel grasper of the system of FIG. 1 in accordance with the disclosure.
Figure 9:
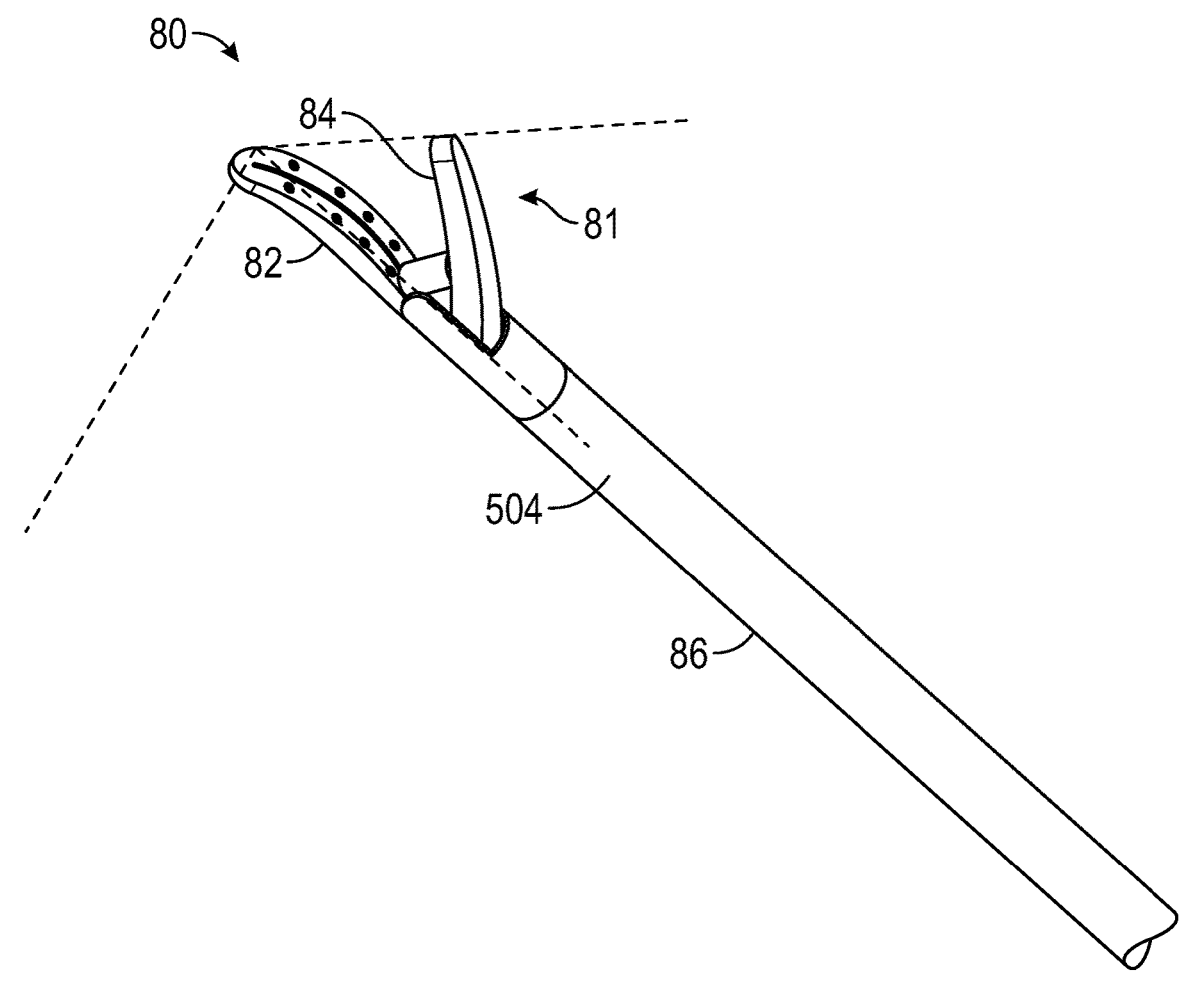
FIG. 9 is a perspective view of the bowel grasper used as a virtual measuring tape in accordance with the disclosure.

With reference being made to FIGS. 8 and 9, a surgical tool 80 configured for operating at the surgical site is shown. The surgical tool 80 defines a central axis. The surgical tool may include a functional extension 81, for example, a bowel grasper, an end effector, a stapler, or a vessel sealer. The functional extension 81 (e.g., end effector) generally includes a shaft 86, a first fixed jaw 84, and a second, moveable jaw 82. The surgical tool 80 may include a fiducial marker 504. Determining a spatial position of the surgical tool 80 may allow determining distances between points along the tissue, or, at least, determining the distance between the tips of the two jaws. Specifically, the lower jaw is fixed, wherein its apex may be considered a fixed point in space, whereas the second jaw is configured to rotate so as to increase/decrease the opening of the jaws.

The surgical tool 80 defines a central axis (see FIG. 8). The surgical tool may include a functional extension, for example, a functional extension 81 (e.g., vessel sealer). In aspects, the vessel sealer 81 includes jaws and disposed thereon, a fiducial marker 504 (FIG. 8). The functional extension 81 may include a first, fixed jaw 84 used as a fixed point and a second, movable jaw 82 (FIG. 8).

Figure 10:
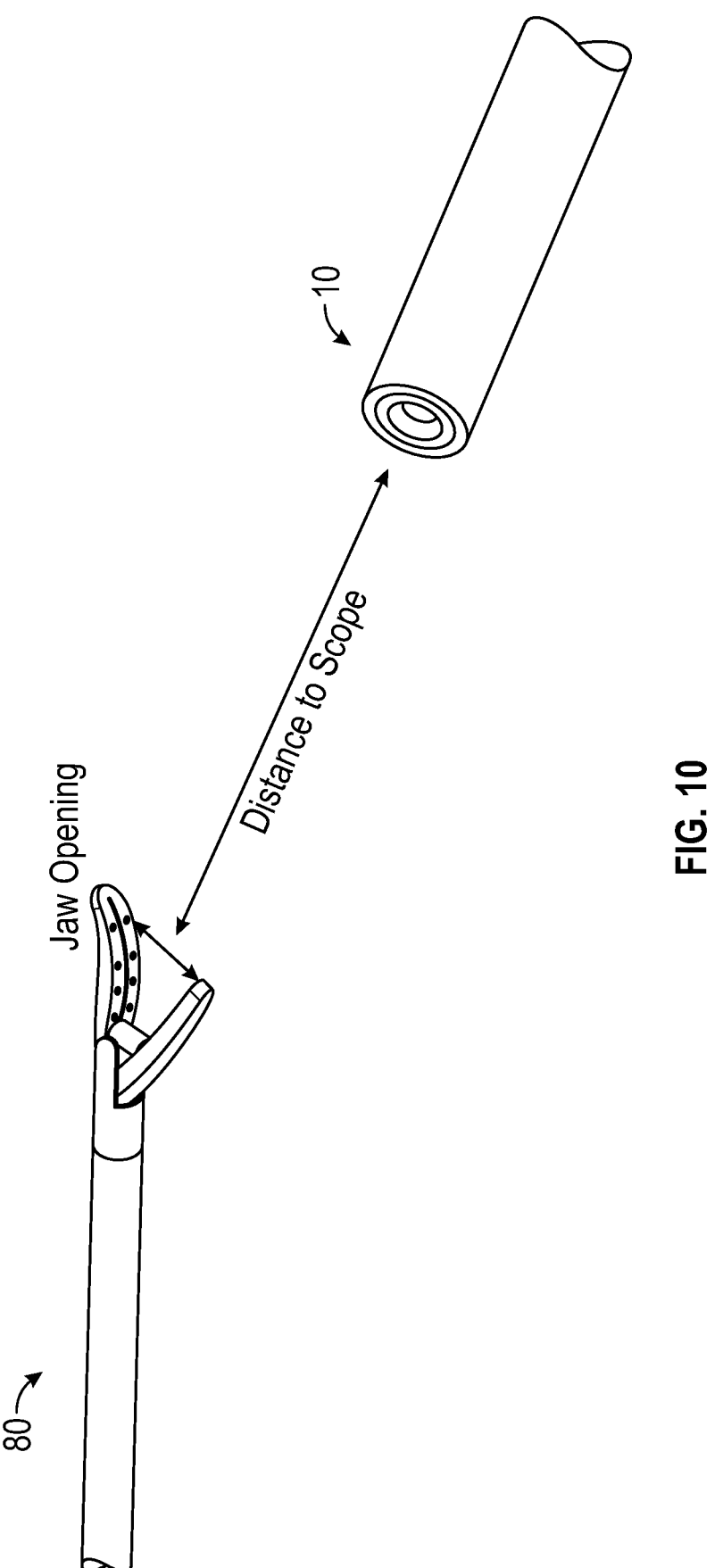
FIG. 10 is a diagram demonstrating measuring the distance between a bowel grasper and a scope, in accordance with the disclosure.

Turning now to FIG. 10, the detection is not limited to the functional extension 81 (e.g., bowel grasper) and may be expanded to other surgical tools as well. For example, the system of the disclosure may be configured for extracting spatial data of the endoscope 10 and, in combination with the detection of the surgical tool 80, allows determining distances and jaw opening.

Figure 11A:
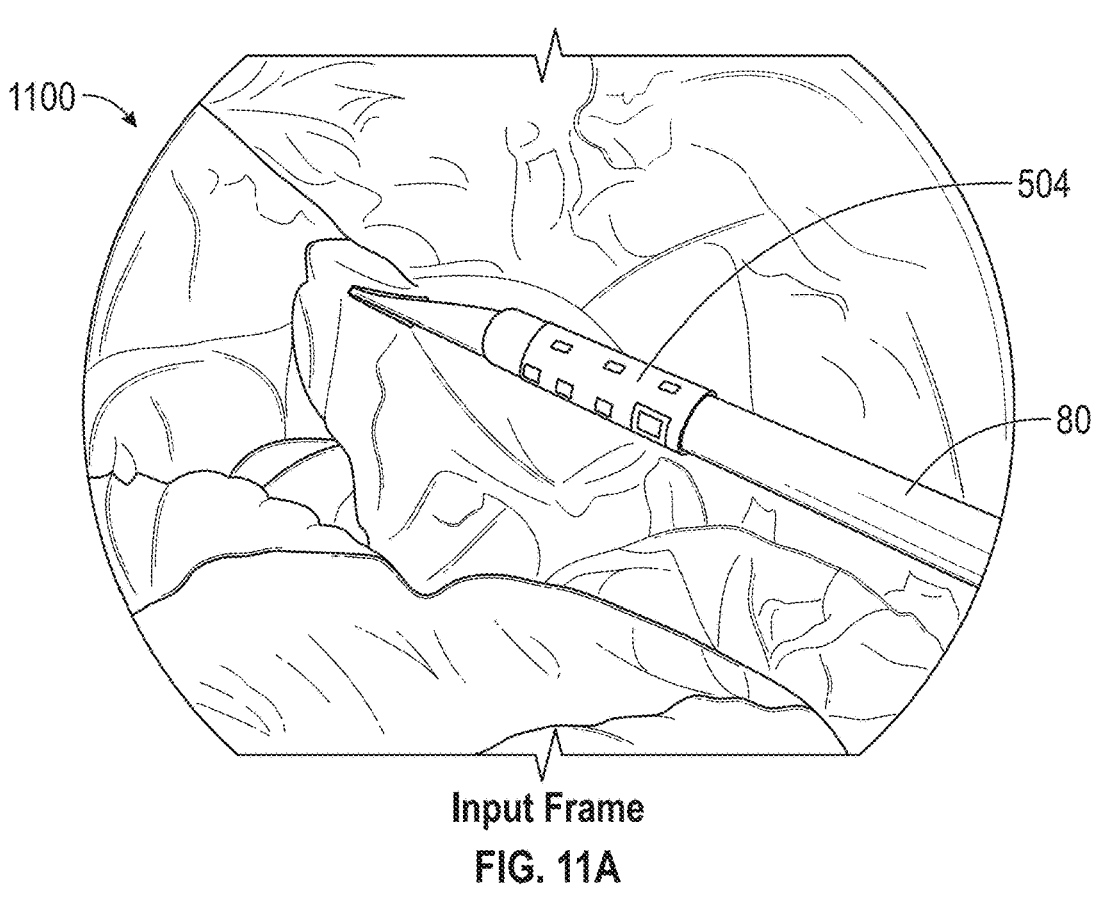
FIG. 11A is a surgical image demonstrating a step of deep learning based on ICG labeling in accordance with the disclosure.
Figure 11B:
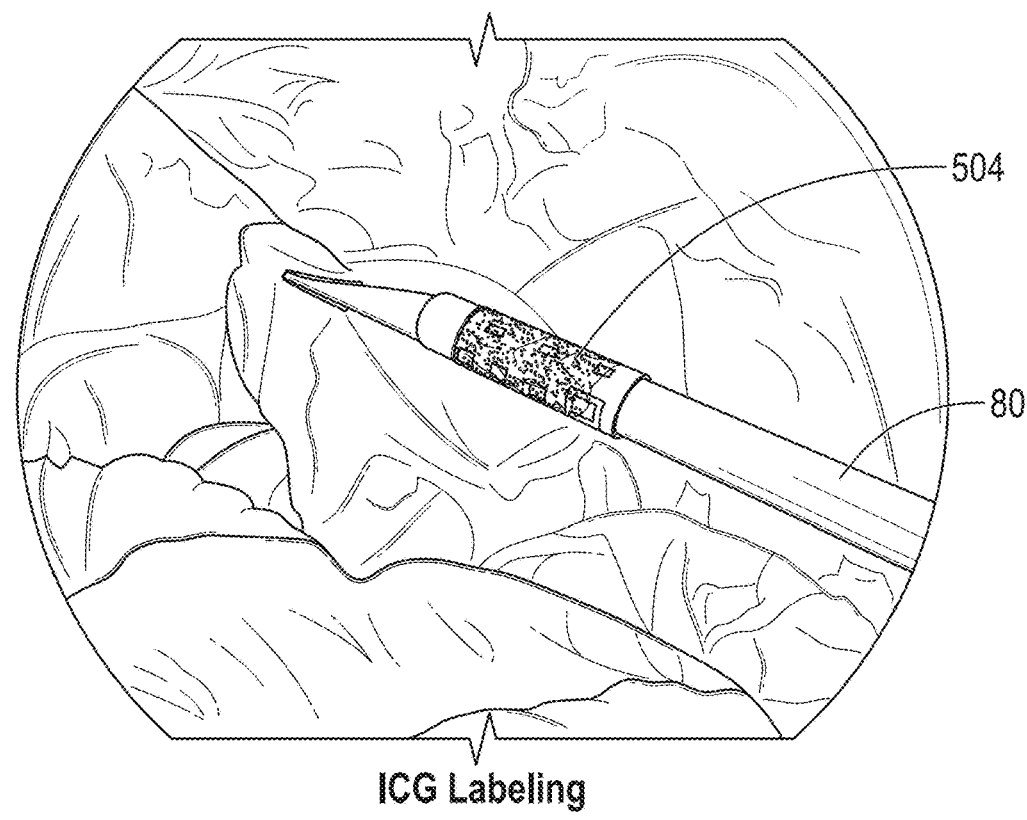
FIG. 11B is a schematic surgical image demonstrating a step of decoding, with classical computer vision, in accordance with the disclosure.

With reference to FIGS. 11A and 11B, labeling of the fiducial marker 504 is shown. Initially, an image 1100 of the surgical site is input into a machine learning network 500 (FIG. 5). The image contains a surgical tool 80. The machine learning network 500 labels the fiducial marker 504. For example, the fiducial marker 504 may be labeled using indocyanine green (ICG) painting (see FIG. 11B). The surgical tool is then imaged, and the region of interest (ROI) of the fiducial marker is predicted.

Next, the video system 30 decodes the image using, for example, but not limited to computer vision, including adaptive thresholding of the ROI, geometric and code constraints on contours in the ROI for detecting the fiducial marker 504, and/or the 2D projection of the surgical tool based on the fiducial marker. This step may provide quite a low false-positive rate, under about 0.1%. A person of ordinary skill in the art would understand computer vision and how to implement it. The computer vision may be performed by the machine learning network 500.

Next, the video system 30 performs 3D reconstruction by solving a Perspective-n-Point (PnP) problem, including providing points on a 3D model and the matched 2D projection, and thereafter solving for the camera positioning. PnP is the problem of estimating the pose of a calibrated camera given a set of 3D points in the world and their corresponding 2D projections in the image.

Figure 12:
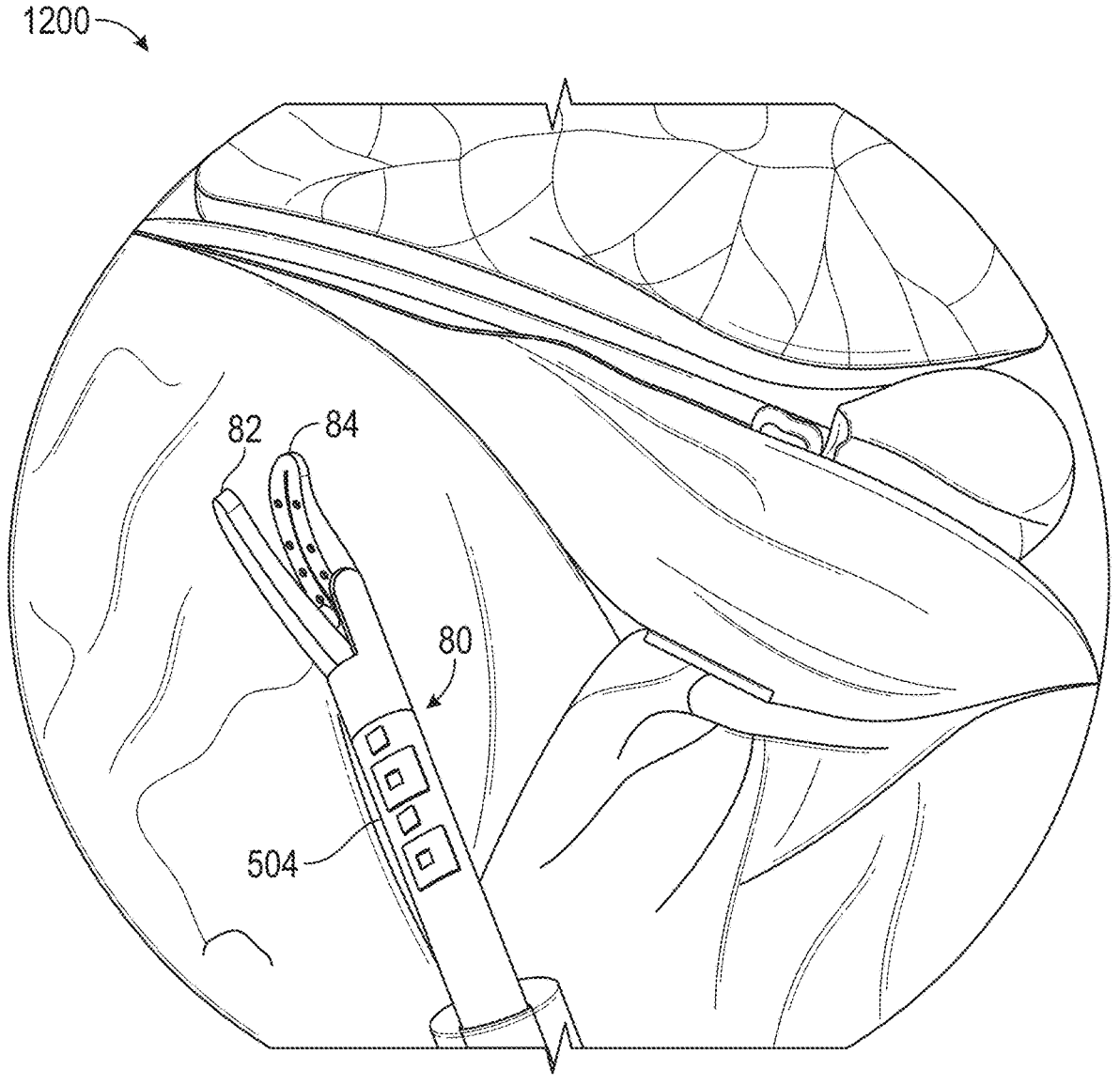
FIG. 12 is a surgical image demonstrating 3D reconstruction in accordance with the disclosure.
Figure 13:
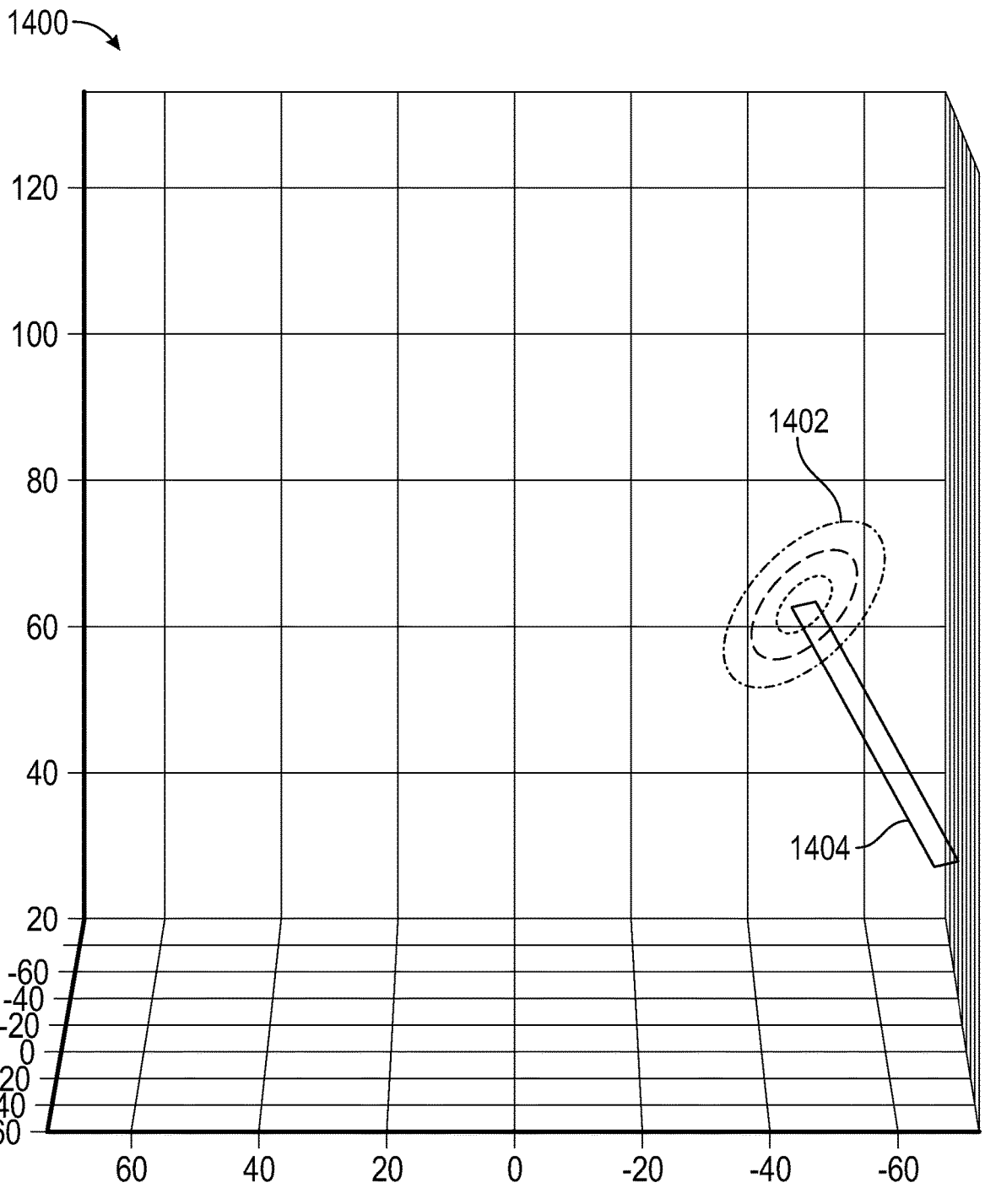
FIG. 13 is a computer model demonstrating 3D reconstruction in accordance with the disclosure.
Figure 14:
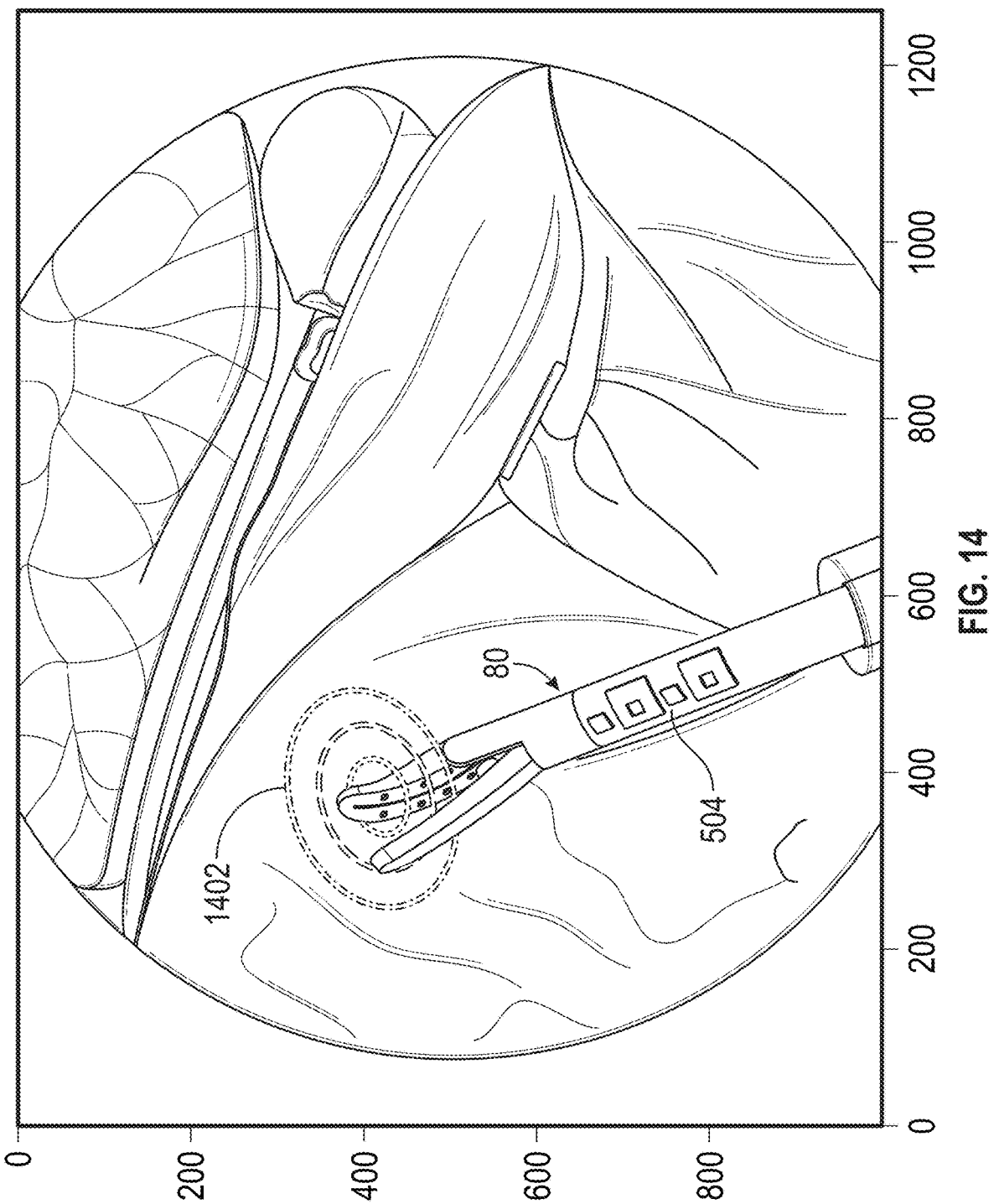
FIG. 14 is a surgical image demonstrating visual augmentation of the surgical tool based on data obtained from the fiducial marker in accordance with the disclosure.

With reference to FIGS. 12 to 14, once the video system 30 determines the orientation of the surgical tool 80 in an image 1200 (FIG. 12) based on the 2D projections, the image may thereafter be augmented by annotations 1402 (FIG. 14) by projecting the computer model onto the images. For example, the video system 30 may determine the orientation of the surgical tool 80 in 3D space (FIG. 13) and determine the location of the annotation 1402 (e.g., a target). The video system 30 may then augment the image using the annotation 1402 (FIG. 14). The annotations may include but are not limited to graphics, text (e.g., an indication of the tool type), one or more colors, and/or patterns (e.g., a series of colored dots).

Figure 15:
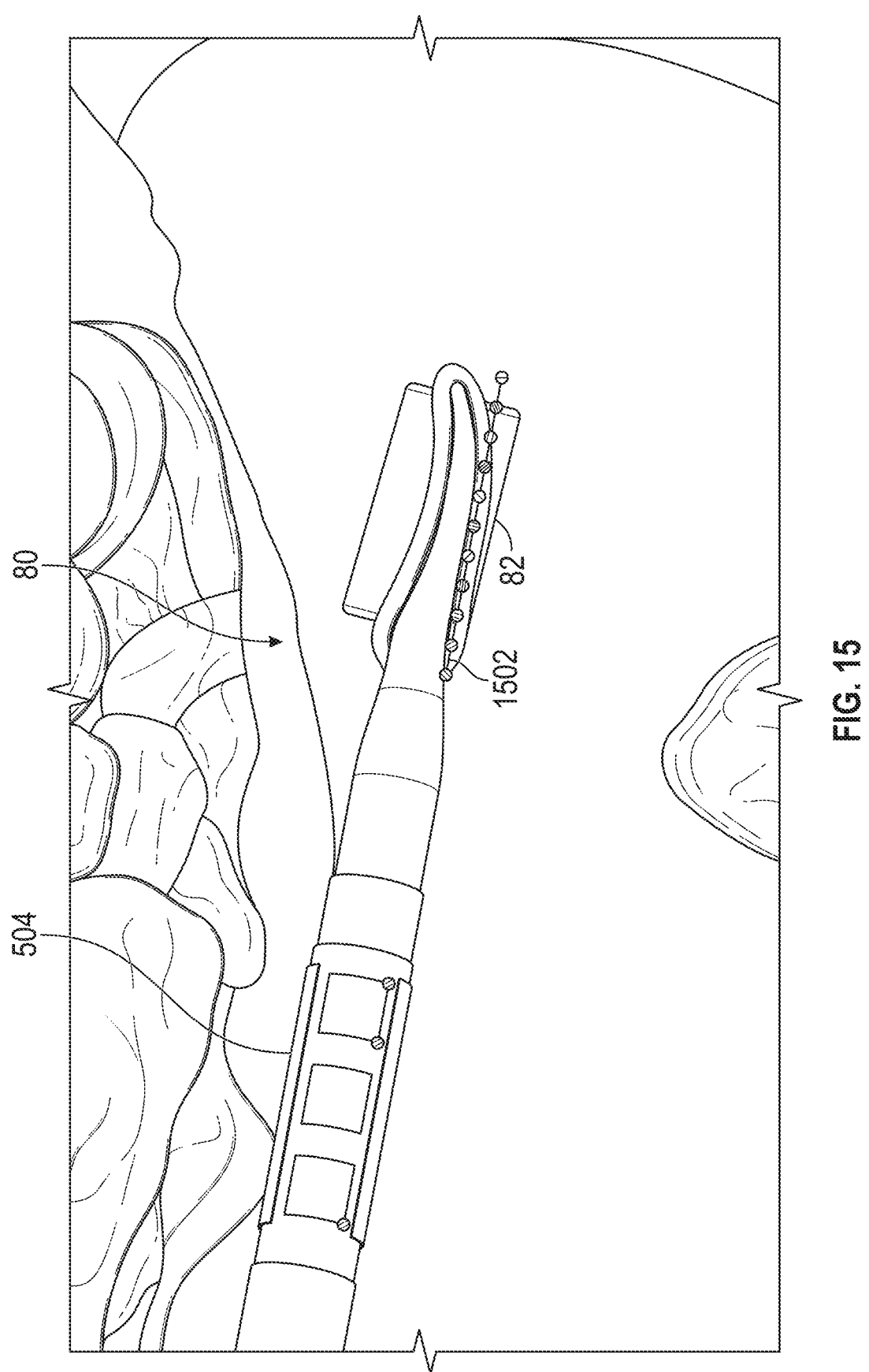
FIG. 15 is an augmented surgical image demonstrating accuracy estimation by predicting the size of known objects, in accordance with the disclosure.

FIG. 15 shows an image augmented to indicate an exemplary augmentation of the image based on the system of the disclosure. The surgical tool 80 has a pattern 1502 overlaid on the moveable jaw 82 of the surgical tool 80 based on the fiducial marker 504.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A spatial orientation dimension and position determining system, comprising:

an imaging device configured for obtaining an image of a surgical site;

a surgical tool configured for operating at the surgical site, the surgical tool including a shaft having a curved outer surface and defining a central axis, and having disposed on the curved outer surface, at least one fiducial marker generated by a machine learning model trained on image data including surgical site images, the machine learning model comprising at least one of a neural network, a convolutional neural network, a recurrent neural network, a generative adversarial network, a Bayesian regression model, a support vector regression model, or a nearest neighbor model, and trained to generate the fiducial marker, such that the at least one fiducial marker includes a distinct pattern extending along the curved outer surface about the central axis, wherein the image of the surgical site reveals only a portion of the fiducial marker;

a processor; and a memory, including instructions stored thereon, which when executed by the processor, cause the spatial dimension and position orientation determining system to:

access an image from the imaging device, the image including at least a portion of the fiducial marker;

determine a spatial positioning of the surgical tool based, at least, on a visible portion of the fiducial marker and the distinct pattern; and determine, based on spatial parameters of the surgical tool, at least one of a position, a dimension, or an orientation of the surgical tool.

2. The spatial orientation determining system according to claim 1, wherein the surgical tool is an endoscopic surgical tool, having a functional extension configured to perform a surgical function, the functional extension including at least one of a grasper, stapler, or vessel sealer, wherein the functional extension includes jaws.

3. The spatial orientation determining system according to claim 2, wherein the instructions, when executed by the processor, further cause the system to:

determine an opening extent of the functional extension based on the determined position, dimension, or orientation of the surgical tool; and determine, based on the opening extent of the jaws of the functional extension, at least one of an amount of tissue pinched between the jaws of the functional extension, or an extent to which the tissue is clamped between the jaws of the functional extension.

4. The spatial orientation determining system according to claim 3, wherein the functional extension has a first, fixed jaw which defines a plane and a second, movable jaw which moves relative to the plane.

5. The spatial orientation determining system according to claim 1, wherein the surgical tool is configured at least for revolution about the central axis, and wherein the instructions, when executed by the processor, further cause the spatial orientation determining system to extract at least any one of the following physical quantities: jaw opening, distance to an endoscope, distances along the shaft, or distances orthogonal to the shaft.

6. The spatial orientation determining system according to claim 1, wherein the fiducial marker includes a fixed point corresponding to a known point of the surgical tool, whereby identifying the portion of the fiducial marker visible to the imaging device allows for the determining of the orientation of the surgical tool.

7. The spatial orientation determining system according to claim 5, wherein the fiducial marker has a unique arrangement of at least one of color, size, clustering, color gradient, or protrusion.

8. The spatial orientation determining system according to claim 1, wherein the fiducial marker comprises a pattern of four-by-four squares of different characteristics.

9. A surgical tool configured for operating at a surgical site, comprising:

a grasper including a shaft defining a central axis and jaws coupled to the shaft and, disposed thereon, at least one fiducial marker generated by a machine learning model trained on image data including surgical site images, the machine learning model comprising at least one of a neural network, a convolutional neural network, a recurrent neural network, a generative adversarial network, a Bayesian regression model, a support vector regression model, a nearest neighbor model, and trained to generate the fiducial marker, such that the at least one fiducial marker includes a distinct pattern extending along a curved outer surface of the shaft about the central axis, wherein an image of the surgical tool reveals only a portion of the at least one fiducial marker, and wherein a visible portion of the at least one fiducial marker is sufficient for determining a spatial positioning of the surgical tool.

10. The surgical tool according to claim 9, wherein the surgical tool further includes at least one functional extension configured to perform a surgical function.

11. The surgical tool according to claim 10, wherein the at least one functional extension is at least one of a bowel grasper, a stapler, or a vessel sealer.

12. The surgical tool according to claim 9, wherein the fiducial marker comprises an image or a pattern configured to be recognizable by a software analyzing the image obtained by an imaging device.

13. The surgical tool according to claim 12, wherein the fiducial marker has a unique arrangement of at least one of color, size, clustering, color gradient, or protrusion.

14. The surgical tool according to claim 9, wherein the fiducial marker comprises a pattern of four-by-four squares of different characteristics.

15. The surgical tool according to claim 9, wherein the fiducial marker is a QR code.

* * * * *